(12) United States Patent
Duhay

(10) Patent No.: US 8,449,565 B2
(45) Date of Patent: May 28, 2013

(54) APPROACHES TO VENOUS OCCLUSION FOR EMBOLUS MANAGEMENT

(76) Inventor: Francis Duhay, Irvine, CA (US)

( * ) Notice: Subject to any disclaimer, the term of this patent is extended or adjusted under 35 U.S.C. 154(b) by 115 days.

(21) Appl. No.: 13/188,408

(22) Filed: Jul. 21, 2011

(65) Prior Publication Data

US 2013/0023909 A1   Jan. 24, 2013

(51) Int. Cl.
*A61B 17/08* (2006.01)

(52) U.S. Cl.
USPC ........... 606/158; 606/194; 606/200; 128/898; 600/504

(58) Field of Classification Search
USPC .......................................... 606/158, 194, 200
See application file for complete search history.

(56) References Cited

U.S. PATENT DOCUMENTS

| | | | |
|---|---|---|---|
| 5,330,451 A | 7/1994 | Gabbay | |
| 5,458,574 A | 10/1995 | Peters | |
| 6,258,120 B1 * | 7/2001 | McKenzie et al. | 623/1.36 |
| 6,451,004 B1 | 9/2002 | Peters | |
| 6,485,500 B1 | 11/2002 | Kokish | |
| 6,558,405 B1 | 5/2003 | McInnes | |
| 6,866,650 B2 | 3/2005 | Stevens | |
| 7,323,001 B2 | 1/2008 | Clubb | |
| 7,896,840 B2 | 3/2011 | Spencer | |
| 7,909,794 B2 | 3/2011 | Briscoe | |
| 7,909,844 B2 | 3/2011 | Alkhabitib | |
| 7,914,643 B2 | 3/2011 | Simpson | |
| 7,951,259 B2 | 5/2011 | Duchamp | |
| 7,959,667 B2 | 6/2011 | Ta | |
| 7,967,781 B2 | 6/2011 | Simpson | |
| 7,972,299 B2 | 7/2011 | Carter | |
| 2003/0162782 A1 | 8/2003 | Grossman | |
| 2004/0122010 A1 | 6/2004 | Grossman | |
| 2004/0172004 A1 | 9/2004 | Mohl | |
| 2005/0055082 A1 | 3/2005 | Ben Muvhar | |
| 2005/0149103 A1 * | 7/2005 | Connors, III | 606/194 |
| 2006/0064059 A1 * | 3/2006 | Gelfand et al. | 604/103.06 |
| 2006/0264759 A1 | 11/2006 | Moehring et al. | |
| 2010/0114299 A1 | 5/2010 | Ben Muvhar | |

FOREIGN PATENT DOCUMENTS

WO   WO 2008/064387   6/2008

OTHER PUBLICATIONS

Davila-Roman, et al. (1999) Atherosclerosis of the ascending aorta is a predictor of renal dysfunction after cardiac operations. Journal of Thoracic and Cardiovascular Surgery. 117:111-116.
Frank and Velden (2011) Cholesterol emboli after coronary bypass surgery. New England J. Medicine. 364:265 (one page only).
Gabrielsen and Norsk (2007) Effect of spaceflight on the subcutaneous venoarteriolar reflex in the human lower leg. J. Appl. Physiol. 103:959-962.
Gao, et al. (2005) Postoperative cognitive dysfunction after cardiac surgery. Chest. 128:3664-3670.
Kooijman, et al. (2007) Local vasoconstriction in spinal cord-injured and able-bodied individuals. J. Appl. Physiol. 103:1070-1077.
Bilecen, et al. (2004) MR Angiography with Venous Compression. Radiology. 233:617-618.

* cited by examiner

*Primary Examiner* — Darwin Erezo
*Assistant Examiner* — Todd J Scherbel
(74) *Attorney, Agent, or Firm* — BakerHostetler

(57) ABSTRACT

The invention provides a method and system for transiently occluding a vein that is downstream of an organ such as the brain, where the occlusion increases blood pressure within the vein, and where the increased pressure stimulates a reflex that reduces entry of emboli into that organ.

29 Claims, 3 Drawing Sheets

APPROACHES TO VENOUS OCCLUSION FOR EMBOLUS MANAGEMENT

FIELD OF THE INVENTION

The present invention relates to methods for reducing or preventing the passage of an embolism into a blood vessel. In particular, the present disclosure offers for consideration novel approaches including venous occlusion for embolus management, for example, for preventing stroke and cardiovascular events during various surgical procedures.

BACKGROUND OF THE INVENTION

Management of emboli has been a prominent issue within the context of the development of new surgical procedures for the last several decades. It is axiomatic that downstream embolus generation constitutes a major drawback within the context of any surgical procedure having a relationship with major organs or organ systems perfused by vessels, wherein diseases or disease states are managed. Minimally invasive techniques have only heightened ongoing awareness of these issues.

There are about 550,000 new strokes in the United States each year. In 1995, stroke mortality was 26.7 per 100,000, or 157,991 deaths. The average cost of care for a patient up to 90 days after a stroke exceeds $15,000. For 10% of patients, the cost of care for the first 90 days after a stroke exceeds $35,000.

A stroke occurs when the nutritive blood flow to part of the brain is suddenly interrupted or when a blood vessel in the brain bursts, spilling blood into the spaces surrounding the brain cells. In the same way that a person suffering a loss of blood flow to the heart is said to be having a heart attack, a person with a loss of blood flow to the brain or sudden bleeding into the brain is said to be having a stroke. Brain cells die when they no longer receive oxygen and nutrients from blood, or when they are damaged by sudden bleeding into or around the brain. Ischemia is the term used to describe the loss of oxygen and nutrients for brain cells when there is inadequate blood flow. Ischemia ultimately leads to infarction, the death of brain cells which are eventually replaced by a fluid-filled cavity, or infarct, in the injured brain.

There are two forms of stroke: hemorrhagic (bleeding into or around the brain), and ischemic (blockage of a blood vessel supplying the brain). Ischemic stroke, in turn, is predominantly associated with three mechanisms: thrombosis of the internal carotid artery: flow-related ischemic events; and cerebral embolism.

Cerebral embolism from the carotid artery lesion is the single most common cause of cerebral ischemic events. Embolism from the atherosclerotic plaque may occur in one of three ways. First, the irregular surface of the plaque is thrombogenic and can accumulate platelet aggregates. If these platelet aggregates become large and embolize to an important cerebral branch, symptoms result. Second, as the atherosclerotic plaque becomes more advanced, it may undergo central degeneration. When this occurs, the plaque may rupture spontaneously, discharging its contents into the lumen of the blood vessel, with subsequent embolism. Third, direct physical trauma to an atherosclerotic plaque or thrombus, as during a carotid endarterectomy operation, may dislodge particulate matter that can embolize to the brain. Regardless of mechanism, the final common pathway of cerebral emboli is mechanical obstruction to nutritive blood flow. The term emboli describes the particles, usually microscopic, that arise from or enter the bloodstream and produce tissue ischemia by lodging within sub-arterial tributaries and depriving tissues of oxygen. Emboli can take the form of blood clots, debris from atherosclerotic plaque, tissue debris from surgery, or air bubbles.

While the layperson is generally aware that atherosclerosis can eventually lead to blood clots that cause heart attacks and stroke, it is also the case that certain medical procedures can provoke emboli and adverse consequences such as stroke and necrosis of tissues distant from the site of formation of the emboli. For example, procedures used in cardiac surgery, such as aortic cannulation, aortic cross-clamping, and proximal coronary artery anastamosis, can disrupt an existing atherosclerotic lesion, provoking emboli taking the form of pieces of the lesion, with consequent stroke. Moreover, these same procedures can provoke the generation blood clots, with the consequent emboli. Emboli that are gas bubbles can arise from medical devices used during cardiopulmonary bypass surgery (Hogue, et al. (2008) Crit. Care Clin. 24:83-89; Falk (2010) European Heart J. 31:278-280). Neurologic complications that are directly linked to embolisms arise during cardiac surgery, where these include transient ischemic attacks, stroke, delirium, coma, and memory deficit (Christenson, et al. (2005) Texas Heart Inst. J. 32:515-521).

Without intending any limitation, the invention provides neurologic embodiments, which include methods for preventing or mitigating stroke, preventing or mitigating transient ischemic attack, preventing or mitigating neurocognitive deficit, and mitigating Alzheimer's disease. Postoperative neurocognitive deficit, which arises from cerebral microemboli, at least in part, can involve impairment of memory, concentration, and language (Gao, et al. (2005) Chest 128:3664-3670, U.S. Pat. No. 7,442,383 issued to Franks, et al; U.S. Pat. Publ. No. 20100173789 of Dambinova). Each of these documents is incorporated herein by reference, as if fully set forth herein. As stated by Gao, et al, neuroprotective therapy "interventions are quite limit." Accordingly, the present invention provides method for preventing or mitigating stroke, neurocognitive deficit, Alzheimer's disease, optionally with the method of administering a neuroprotecting agent, such as a anti-inflammatory agent. Neuroprotecting agents of the present invention encompass aprotinin, heparin coating of cardiopulmonary bypass (CPB) circuits, barbiturates, xenon gas, and steroids (Gao, et al. (2005) Chest 128:3664-3670).

Additionally, cardiac operations, aortic operations, and aortic instrumentation result in high risk for an embolism or emboli that have pathological consequences on organs other than the brain. For example, cardiac surgery can result in acute renal failure, attributed to embolisms of atherosclerotic material to the kidneys (Davila-Roman, et al. (1999) J. Thorac. Cardiovasc. Surg. 117:111-116). Cardiac surgery can result in pulmonary embolisms (Goldhaber and Schoepf (2004) Circulation 109:2712-2715). Cardiac surgery can also result in pathological embolisms to the extremities (Frank and Velden (2011) New Engl. J. Med. 364:265). Aortic instrumentation encompasses wires, aortic angiography, and a delivery system for a stent graft.

Renal embodiments are provided. Abdominal aortic aneurysms cause about 6000 deaths per year in England and Wales (Symons and Gibbs (2009) Br. J. Hosp. Med. (Lond.) 70:566-571). An abdominal aortic aneurysm (AAA) can treated using an stent, where the stent is sometimes known as a "triple A stent." Stents used for treating AAA are disclosed (see, e.g., Goncalves, et al. (2010) J. Cardiovasc. Surg. (Torino) 51:515-531; Mastracci (2010) Perspect. Vasc. Surg. Endovasc. Ther. 22:214-218; Choong, et al. (2010) Surgeon 8:28-38). With placement of the stent in the thoracic aorta, and the top end of the stent can be situated somewhat above the renal artery, and the bottom end of the stent can be situated somewhat just beyond the lower surface of the aneurysm, with the body of the stent extending through the entire aneurysm. The installation of the stent, and related mechanical or surgical procedures, can produce emboli, where the emboli can enter the renal artery and, once in the renal artery, travel to the kidneys and cause renal damage. The method of the present invention occludes the renal vein, thereby causing a venoarterial reflex that contracts part of the renal artery, thereby directing emboli away from the kidneys, and instead down the abdominal aorta and towards the legs. The renal embodiment of the inventive method optionally encompasses at least one filter, at least one anticoagulant or thrombolytic agent, the surgery that installs the stent, and any medical procedure for diagnosing the aneurysm. In another aspect, the renal embodiment of the method does not encompass the surgery that installs the stent, or does not include any medical procedure for diagnosing the aneurysm. See, for example, U.S. Pat. No. 6,558,405, issued to McInnes which is incorporated by reference herein in its entirety.

Devices are available for protecting against embolisms, particularly filters and/or baskets, however such devices have only highlighted or underscored the amount of thrombus present in any given procedures. Further, it is noted that where these include balloon occlusion devices and filter devices, intrinsic limitations and the protection has been characterized as being far from complete (Sangiorgi and Columbo (2003) Heart 89:990-992). Inflation of a balloon can be with an air, a fluid such as saline, a gel, and the like. Inflation encompasses partial inflation, optimal inflation, maximal inflation, and complete inflation, unless expressly stated otherwise or dictated otherwise by the context. Deflation encompasses partial deflation or complete deflation, unless expressly stated otherwise, or dictated otherwise by the context.

The present invention takes a new approach by occluding the blood flow in a blood vessel leaving an organ, that is, a vein, where the occlusion re-directs blood entering the organ away from the organ, and where the re-direction takes advantage of the venoarterial reflex. By re-directing the emboli, and by preventing passage of the emboli through the occluded vein, the invention mitigates, extenuates, or in some cases, prevents stroke. Accordingly, there exists a longstanding need to address and manage thrombi. Prior to the instant teachings, a large gap existed.

SUMMARY OF THE INVENTION

The present invention provides a method for reducing the flow of blood entering an organ or tissue, comprising transiently occluding a vein that carries blood out of the organ or tissue, wherein the occluding raises the blood pressure in the vein, wherein the raise in blood pressure stimulates a venoarterial reflex, and wherein the reflex reduces the passage of blood through an artery or arteriole entering the organ or tissue, and re-directs blood away from the organ or tissue.

In another aspect, the method includes an embodiment wherein the artery or arteriole comprises at least one embolus, and wherein the method re-directs the at least one embolus away from the organ or tissue.

Furthermore, the invention provides the above method, wherein the occluding comprises a device, wherein the device comprises a non-porous material, and wherein the device is non-porous to blood flowing from the upstream side of the device to the downstream side of the device.

In another aspect, what is provided is the above method, wherein the occluding is accomplished with a balloon located in the lumen of the vein, a device comprising an occluding cuff located in the lumen of the vein, a device that clamps the outside of the vein, manual contact that presses on the outside of the vein, or a tourniquet that constricts a limb.

The above method includes an embodiment wherein the occluding is not accomplished with a device comprising a balloon. Moreover, what is embraced is the above method, wherein the artery or arteriole comprises at least one embolus, and wherein the method re-directs the at least one embolus away from the organ or tissue, and wherein the embolus comprises a blood clot, a fragment of atherosclerotic plaque, debris from surgery, a gas bubble, a synthetic microsphere, or an iatrogenic consequence of a medical procedure.

In yet another aspect, what is contemplated is the above method that further includes a medical procedure that comprises carotid endarterectomy, cardioversion for atrial fibrillation, repair of thoracic aortic aneurysm, coronary artery bypass grafting, aortic valve surgery, mitral valve surgery, clamp removal, or iatrogenic physical trauma to the cardiovascular system. Moreover, the method can be practiced, where the artery comprises a saphenous vein graft. And the method can be practiced, wherein the organ is the brain or kidney.

Moreover, what is embraced is the above method that comprises transient occluding of the superior vena cava or jugular vein, wherein the venoarterial reflex constricts blood flow in one or more of the aorta, subclavian artery, brachiocephalic artery, subclavian artery, and reduces blood flow to the brain.

Yet another aspect of the invention, is the above method, wherein the occluding is accomplished with a device comprising a non-porous material that is non-porous to blood flowing from the upstream side of the device to the downstream side of the device, wherein the device is located in the lumen of a vein downstream of the heart, wherein blood flow in the vessel introduces an instability of the position or fit of the device within the lumen, and wherein the method further comprises stabilizing the device by fibrillating the heart or by reducing the volume or rate of the blood flow that enters the heart.

Moreover, what is contemplated is the above method, that comprises transient occluding of the renal vein, wherein a venoarterial reflex constricts blood flow in the aorta, and wherein the reflex reduces blood flow, or blood flow and at least one embolus, to at least one kidney. Additionally, the method finds use wherein there is a region of occlusion or a point of occlusion created by the occluding a vein, wherein the method further includes use of a gauge that monitors blood pressure in a region of the circulatory system between the organ and the region or point of occlusion. In another aspect of the invention, the method comprises use of an occluding balloon that transiently occludes the vein, wherein the balloon is coupled to a controller that monitors venous pressure, and wherein the controller deflates the balloon if the pressure is too high or inflates the balloon if the pressure is too low.

In a valve embodiment, the invention provides the above method, that includes using a pressure safety-release valve for reducing venous pressure if the pressure is too high. In a monitor embodiment, the invention contemplates the above method that includes a monitor that monitors the frequency of emboli, and wherein there is a controller that controls a balloon that occludes a vein, wherein the controller substantially maintains inflation of the balloon, or increases inflation of the balloon, when the controller detects an elevated frequency of emboli.

In a filter embodiment, the present invention encompasses using, maintaining, or implanting, a filter in an artery or vein that traps emboli, or administering an anti-coagulant or thrombolytic agent.

In embodiment of the present invention that reduces emboli, what is provided is a method for reducing the passage of emboli into an organ or tissue, comprising transiently occluding a vein that carries blood out of the organ or tissue, wherein the occluding raises the blood pressure in the vein, wherein the raised blood pressure in the vein stimulates a venoarterial reflex that constricts an artery or arteriole carrying blood, or blood and emboli, into the organ or tissue, resulting in a re-directing of blood, or blood and emboli, away from the organ or tissue and through at least one artery or arteriole that does not carry blood to the organ or tissue.

In another aspect, the method includes an embodiment wherein the artery or arteriole comprises at least one embolus, and wherein the method re-directs the at least one embolus away from the organ or tissue.

Furthermore, the invention provides the above method, wherein the occluding comprises a device, wherein the device comprises a non-porous material, and wherein the device is non-porous to blood flowing from the upstream side of the device to the downstream side of the device.

In another aspect, what is provided is the above method, wherein the occluding is accomplished with a balloon located in the lumen of the vein, a device comprising an occluding cuff located in the lumen of the vein, a device that clamps the outside of the vein, manual contact that presses on the outside of the vein, or a tourniquet that constricts a limb.

The above method includes an embodiment wherein the occluding is not accomplished with a device comprising a balloon. Moreover, what is embraced is the above method, wherein the artery or arteriole comprises at least one embolus, and wherein the method re-directs the at least one embolus away from the organ or tissue, and wherein the embolus comprises a blood clot, a fragment of atherosclerotic plaque, debris from surgery, a gas bubble, a synthetic microsphere, or an iatrogenic consequence of a medical procedure.

In yet another aspect, what is contemplated is the above method that further includes a medical procedure that comprises carotid endarterectomy, cardioversion for atrial fibrillation, repair of thoracic aortic aneurysm, coronary artery bypass grafting, aortic valve surgery, mitral valve surgery, clamp removal, or iatrogenic physical trauma to the cardiovascular system.

Moreover, the method can be practiced, where the artery comprises a saphenous vein graft. And the method can be practiced, wherein the organ is the brain or kidney. Moreover, what is embraced is the above method that comprises transient occluding of the superior vena cava or jugular vein, wherein the venoarterial reflex constricts blood flow in one or more of the aorta, subclavian artery, brachiocephalic artery, subclavian artery, and reduces blood flow to the brain.

Yet another aspect of the invention, is the above method, wherein the occluding is accomplished with a device comprising a non-porous material that is non-porous to blood flowing from the upstream side of the device to the downstream side of the device, wherein the device is located in the lumen of a vein downstream of the heart, wherein blood flow in the vessel introduces an instability of the position or fit of the device within the lumen, and wherein the method further comprises stabilizing the device by fibrillating the heart or by reducing the volume or rate of the blood flow that enters the heart. Moreover, what is contemplated is the above method, that comprises transient occluding of the renal vein, wherein a venoarterial reflex constricts blood flow in the aorta, and wherein the reflex reduces blood flow, or blood flow and at least one embolus, to at least one kidney.

Additionally, the method finds use wherein there is a region of occlusion or a point of occlusion created by the occluding a vein, wherein the method further includes use of a gauge that monitors blood pressure in a region of the circulatory system between the organ and the region or point of occlusion. In another aspect of the invention, the method comprises use of an occluding balloon that transiently occludes the vein, wherein the balloon is coupled to a controller that monitors venous pressure, and wherein the controller deflates the balloon if the pressure is too high or inflates the balloon if the pressure is too low.

In a valve embodiment, the invention provides the above method, that includes using a pressure safety-release valve for reducing venous pressure if the pressure is too high. In a monitor embodiment, the invention contemplates the above method that includes a monitor that monitors the frequency of emboli, and wherein there is a controller that controls a balloon that occludes a vein, wherein the controller substantially maintains inflation of the balloon, or increases inflation of the balloon, when the controller detects an elevated frequency of emboli.

In a filter embodiment, the present invention encompasses using, maintaining, or implanting, a filter in an artery or vein that traps emboli, or administering an anti-coagulant or thrombolytic agent.

In a neurological embodiment of the present invention, what is provided is a method for preventing or mitigating emboli-dependent stroke, ischemic attack, neurocognitive deficit, or Alzheimer's disease, comprising transiently occluding a vein that delivers blood to the brain, wherein the occluding raises blood pressure in the vein, wherein the raised blood pressure in the vein stimulates a venoarterial reflex that constricts an artery that delivers blood to the brain, resulting in a re-directing of emboli away from the brain and to the extracranial systemic circulation. In another aspect, what is provided is the above method, wherein the vein is the superior vena cava or jugular vein. In a further aspect of the neurological embodiment, what is provided is the above method, wherein the vein is not the superior vena cava and not the jugular vein. Moreover, the above method provides an embodiment wherein the artery or arteriole comprises the carotid artery or an intracranial artery of the brain.

In another aspect of the neurological embodiment, what is provided is a method for preventing or mitigating emboli-dependent stroke, ischemic attack, neurocognitive deficit, or Alzheimer's disease, comprising transiently occluding a vein that delivers blood to the central nervous system, wherein the occluding raises blood pressure in the vein, wherein the raised blood pressure in the vein stimulates a venoarterial reflex that constricts an artery that delivers blood to the brain, resulting in a re-directing of emboli away from the central nervous system and to circulation that is not part of the central nervous system.

In another aspect, the method includes an embodiment wherein the artery or arteriole comprises at least one embolus, and wherein the method re-directs the at least one embolus away from the brain, central nervous system, organ, or tissue.

Furthermore, the invention provides the above method, wherein the occluding comprises a device, wherein the device comprises a non-porous material, and wherein the device is non-porous to blood flowing from the upstream side of the device to the downstream side of the device.

In another aspect, what is provided is the above method, wherein the occluding is accomplished with a balloon located in the lumen of the vein, a device comprising an occluding cuff located in the lumen of the vein, a device that clamps the outside of the vein, manual contact that presses on the outside of the vein, or a tourniquet that constricts a limb.

The above method includes an embodiment wherein the occluding is not accomplished with a device comprising a balloon. Moreover, what is embraced is the above method, wherein the artery or arteriole comprises at least one embolus, and wherein the method re-directs the at least one embolus away from the organ or tissue, and wherein the embolus comprises a blood clot, a fragment of atherosclerotic plaque, debris from surgery, a gas bubble, a synthetic microsphere, or an iatrogenic consequence of a medical procedure.

In a therapeutic embodiment, the above method comprises administering a drug, microsphere bearing a drug or radioisotope, or a medical device configured for passage in the bloodstream, and occluding a vein, where a venoarterial reflex constricts an artery thereby re-directing blood, and where the re-directing of the blood also re-directs the drug or medical device to a therapeutically relevant part of circulatory system. In a diagnostic embodiment, for example involving an antibody, a metabolite, a microsphere, or a medical device configured for passage in the bloodstream, the method comprises administering the diagnostic, and occluding a vein, where a venoarterial reflex constricts an artery thereby re-directing blood, and where the re-directing of the blood also re-directs the diagnostic to a diagnostically relevant part of the circulatory system. In a subject administered a pharmaceutical or diagnostic, the invention comprises occluding a vein, where the occluding results in a venoarterial reflex that constricts arterial flow (in this embodiment, the invention does not encompass the step of administering, but only requires that the subject be administered). In one aspect of the invention, the subject is administered the pharmaceutical or diagnostic before initiating the occluding. In another aspect of the invention, the subject is administered a pharmaceutical or diagnostic after initiating the occluding. In yet another embodiment, the subject is administered a pharmaceutical or diagnostic concurrently with initiating the occluding.

The present invention further includes a system for reducing the flow of blood entering an organ or tissue, comprising transiently occluding a vein that carries blood out of the organ or tissue, wherein the occluding raises the blood pressure in the vein, wherein the raise in blood pressure stimulates a venoarterial reflex, and wherein the reflex reduces the passage of blood through an artery or arteriole entering the organ or tissue, and re-directs blood away from the organ or tissue. Without limitation, the system can comprise a machine, a computer, a monitor, a power supply, a display, and any combination thereof, In another aspect, the invention comprises the above system, wherein the device monitors or detects the generation, release, or number, of emboli.

The above-disclosed system includes an embodiment, wherein the artery or arteriole comprises at least one embolus, and wherein the method re-directs the at least one embolus away from the organ or tissue.

In an alternate aspect, the above system includes an embodiment wherein the occluding comprises a device, wherein the device comprises a non-porous material, and wherein the device is non-porous to blood flowing from the upstream side of the device to the downstream side of the device.

The above system further includes an embodiment, wherein the occluding is accomplished with a balloon located in the lumen of the vein, a device comprising an occluding cuff located in the lumen of the vein, a device that clamps the outside of the vein, manual contact that presses on the outside of the vein, or a tourniquet that constricts a limb.

Moreover, what is contemplated is the above system, wherein the occluding is not accomplished with a device comprising a balloon.

In the above system, what is embraced is an embodiment wherein the artery or arteriole comprises at least one embolus, and wherein the method re-directs the at least one embolus away from the organ or tissue, and wherein the embolus comprises a blood clot, a fragment of atherosclerotic plaque, debris from surgery, a gas bubble, a synthetic microsphere, or an iatrogenic consequence of a medical procedure.

Regarding the above system, what is encompassed is an embodiment that further includes a medical procedure that comprises carotid endarterectomy, cardioversion for atrial fibrillation, repair of thoracic aortic aneurysm, coronary artery bypass grafting, aortic valve surgery, mitral valve surgery, clamp removal, or iatrogenic physical trauma to the cardiovascular system.

The system also comprises an embodiment, where the artery comprises a saphenous vein graft. What is additionally contemplated, is the above system wherein the organ is the brain or kidney. Furthermore, the above system comprises transient occluding of the superior vena cava or jugular vein, wherein the venoarterial reflex constricts blood flow in one or more of the aorta, subclavian artery, brachiocephalic artery, subclavian artery, and reduces blood flow to the brain.

In yet another aspect, the present system includes an embodiment wherein the occluding is accomplished with a device comprising a non-porous material that is non-porous to blood flowing from the upstream side of the device to the downstream side of the device, wherein the device is located in the lumen of a vein downstream of the heart, wherein blood flow in the vessel introduces an instability of the position or fit of the device within the lumen, and wherein the method further comprises stabilizing the device by fibrillating the heart or by reducing the volume or rate of the blood flow that enters the heart.

Also embraced, is the above system that comprises transient occluding of the renal vein, wherein a venoarterial reflex constricts blood flow in the aorta, and wherein the reflex reduces blood flow, or blood flow and at least one embolus, to at least one kidney.

Additionally, the system includes is a region of occlusion or a point of occlusion created by the occluding a vein, wherein the method further includes use of a gauge that monitors blood pressure in a region of the circulatory system between the organ and the region or point of occlusion.

What is also embraced, is the above system that comprises use of an occluding balloon that transiently occludes the vein, wherein the balloon is coupled to a controller that monitors venous pressure, and wherein the controller deflates the balloon if the pressure is too high or inflates the balloon if the pressure is too low.

Moreover, the system includes using a pressure safety-release valve for reducing venous pressure if the pressure is too high.

In another aspect, the system includes a monitor that monitors the frequency of emboli, and wherein there is a controller that controls a balloon that occludes a vein, wherein the controller substantially maintains inflation of the balloon, or increases inflation of the balloon, when the controller detects an elevated frequency of emboli.

The present system, further comprises using, maintaining, or implanting, a filter in an artery or vein that traps emboli, or administering an anti-coagulant or thrombolytic agent.

Figure 1:
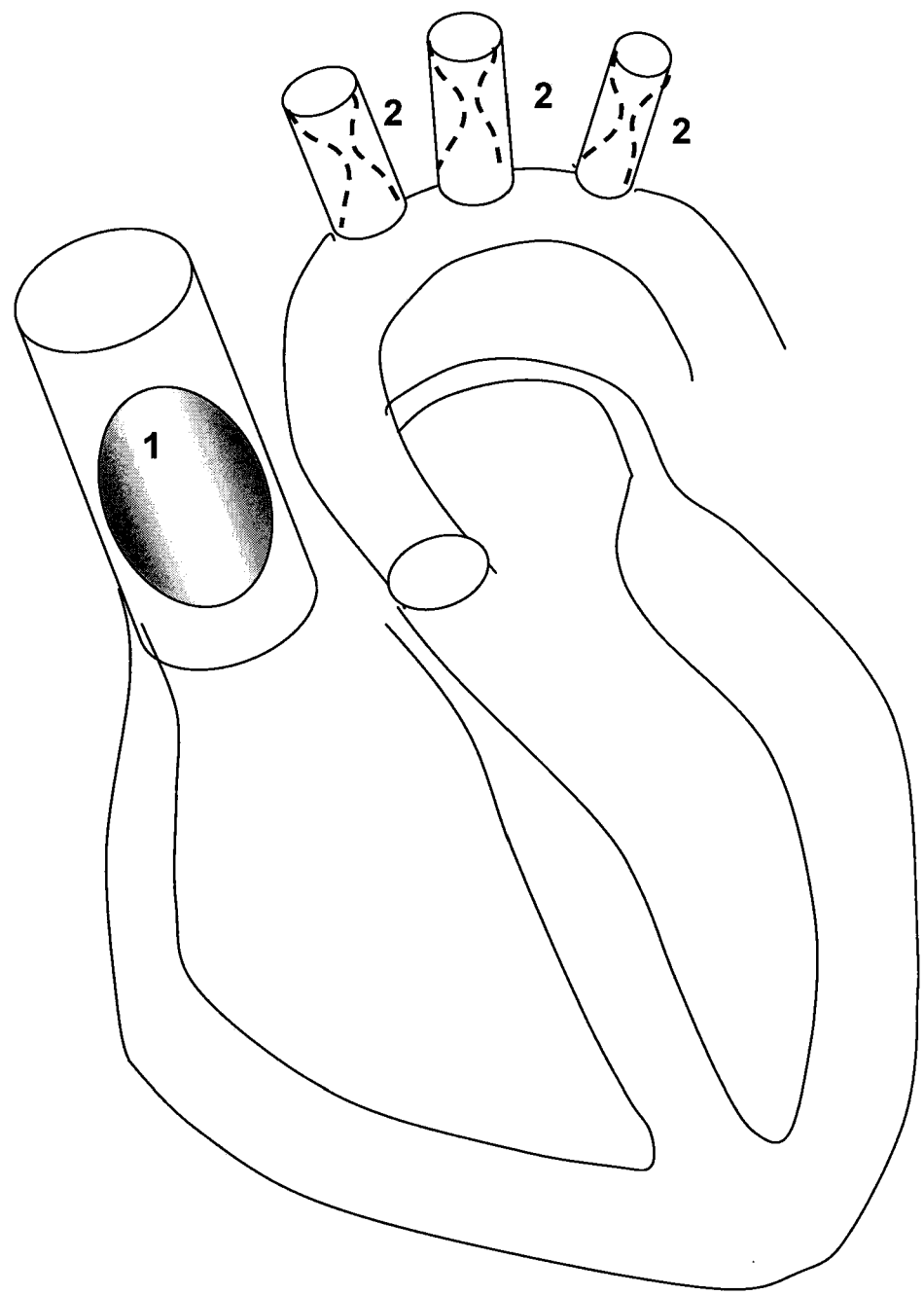
FIG. 1. Venoarterial reflex preventing stroke in brain. (1) Occluding balloon resides in superior vena cava. The occlusion increases blood pressure, where this increase causes venoarterial reflex; (2) Venoarterial reflex provokes contraction of one or more arteries leading to the brain.

As used herein, including the appended claims, the singular forms of words such as "a," "an," and "the" include their corresponding plural references unless the context clearly dictates otherwise. All references cited herein are incorporated by reference to the same extent as if each individual publication, patent, and published patent application, as well as figures and drawings in said publications and patent documents, was specifically and individually indicated to be incorporated by reference.

The present inventor has discovered novel enhanced approaches to thrombus management which address and solve longstanding needs, and overcome paucity of extant clinical solutions.

By way of definition, occluding a vessel refers to stopping or blocking greater than 99% of the blood flow. Constricting a vessel encompasses partially reducing blood flow as well as occluding blood flow. Venoarterial reflex and venoarteriolar reflex refer to the same type of reflex, where the former refers to a reflex in an artery and the latter refers to a reflex in an arteriolar. Upstream refers to a direction or movement against the flow of blood in a vessel of the circulatory system. Downstream refers to a direction or movement with the flow of blood, that is, in the same direction as the movement of blood in a vessel of the circulatory system. A method or system where an occluding comprises a device, encompasses the following. Where an "occluding comprises a device," or where an "occlusion that comprises a device," and the like, what is encompassed without limitation is a device that occupies a position in the bloodstream and where the device directly obstructs the passage of blood. What is also encompassed by an "occluding comprises a device," or an "occlusion that comprises a device," and the like, and without limitation, is a device that clamps the outside of blood vessel to occlude blood flow, but does not come in direct contact with the contact with the blood.

Without implying any limitation, blood that is "upstream" to a device may be "immediately upstream" to the device. Alternatively, blood that is "upstream" to a device is characterized in that the hemoglobin content, oxygen concentration, and carbon dioxide concentration, are essentially the same as blood that contacts the device. In another aspect, blood that is "upstream" to a device is characterized in that no major arteries or veins branch from the vessel in the region between the upstream blood and the device. Without limitation, blood that is "downstream" to a device may be "immediately downstream" to the device. In another non-limiting aspect, blood that is "downstream" to a device is characterized in that the hemoglobin content, oxygen concentration, and carbon dioxide concentration, of the blood are essentially the same as blood that contacts the device. In another aspect, blood that is "downstream" to a device is characterized in that no major arteries or veins branch from the vessel in the region between the downstream blood and the device.

The following provides an example of the venoarterial reflex involving the arm or leg. Increase in venous blood pressure stimulates the venoarteriolar reflex, as disclosed by Robertson (Robertson (2004) *Venoarteriolar Reflex* by P. A. Low in *Primer on the Autonomic Nervous System*, Academic Press, San Diego, Calif., pp. 52-53). The venoarteriolar reflex helps maintain stable blood flow when there are changes in a person's posture. When only a limb is moved, for example, venous transmural pressure can increase by 0.025 mm Hg. This increase in venous pressure can occur when lowering a limb. This increase in pressure causes a reduction in blood flow, where this reduction takes the form of an abrupt reduction in blood flow of about 50%. This is the venoarteriolar reflex. Without intending any limitation on the invention, this reflex occurs in all tissues of the limbs, including subcutaneous adipose tissue, muscle, and skin (Robertson, supra). See also, e.g., Kooijman, et al. (2007) J. Appl. Physiol. 103:1070-1077; Gabrielsen and Norsk (2007) J. Appl. Physiol. 103: 959-962; and Bjerre-Jepsen, et al. (1983) Clin. Physiol. 3:29-33. Venoarterial reflex can be detected, for example, by a laser Doppler method (see, e.g., Stoyneva (2004) Auton. Neurosci. 116:62-68).

The invention provides transient or intermittent inflation of an intravenous balloon before arterial manipulations, for example, manipulations on the aorta. The intravenous balloon can reside in a vein, for example, the superior vena cava or jugular vein, where inflation raises the blood pressure within that vein. In general, the vein chosen for balloon occlusion depends on the proximate tissue or organ bed most vulnerable to embolic infarction, or associated with the greatest risk of patient morbidity or mortality. The increased blood pressure in the vein provides a venoarterial reflex, which exerts its effect on the carotid artery and intracranial arteries of the brain.

The result is that any emboli generated during cardiovascular surgery are directed away from the brain, and instead enter the extracranial systemic circulation. Where the method of the invention is applied to a vein leaving the brain, cerebral perfusion is transiently reduced. This transient reduction arises from two effects, namely, from: (1) Venous flow restriction by the balloon, or other device; and (2) Arterial constriction by the venoarterial reflex. To prevent adverse effects on the brain, the method of the present invention is applied transiently, for example, at an interval lasting several seconds where this interval coincides with the expected duration or interval of release of emboli.

The invention takes advantage of the venoarterial reflex or venoarteriolar reflex, where occlusion of a vein exiting an organ transmits a signal to an artery entering the same organ, and re-directs blood away from that organ to other blood vessels. In an article entitled, "How do veins talk to arteries?" it is disclosed that the venoarterial reflex occurs in a number of organs and tissues, including muscle, the limbs, subcutaneous adipose tissue, and limbs (Johnson (2002) J. Physiol. 538:341).

The invention optionally encompasses a step that measures a venoarterial reflex or venoarteriolar reflex. This reflex can be measured, for example, by assessing contraction of the relevant artery or arteriole. What can be measured, for example, is the diameter of the constricted blood vessel, and patterns of construction, such as a bead-string pattern. In vivo measurement of various parameters of an artery can be accomplished by video microscopy (Laemmel, et al. (2003) Am. J. Physiol. Circ. Physiol. 285:H1254-H1260; Morris (1999) Am. J. Physiol. 277:H58-H64), a plethysmographic technique (Strachan, et al. (2000) Br. J. Clin. Pharmacol. 50:27-30; Snapir, et al. (2009) Br. J. Anaesthesia 102:38-46); orthogonal polarization spectral imaging (OPS) (Pennings, et al. (2004) Stroke 35:1284-1288); fluorescent intravital microscopy (Brookes and Kaufman (2005) J. Physiol. 565: 269-277), magnetic resonance angiography (MRA) (Kitamura, et al. 2009) Plos One 4:e5159 (13 pages), and the like.

Regions of the circulatory system that are subject to a venoarterial reflex can be detected and the reflex that is inherent in the region can be characterized. In one aspect, a region of the circulatory system refers to the combination of an artery upstream of an organ or tissue and a vein downstream of the same organ or tissue. In another aspect, a region of the circulatory system refers to the combination of an artery immediately upstream of an organ or tissue and a vein immediately downstream of the same organ or tissue. In yet another aspect, a region of the circulatory system refers to the combination of a region of an artery that is inside an organ or tissue, and a vein that is inside of the same organ or tissue. The present invention embraces combinations, such as an artery that is embedded in an organ or tissue, and a vein immediately downstream of the same organ or tissue.

In one embodiment, the invention provides a method and a system for occluding a vein that transports venous blood from the brain, activating a venoarterial reflex that constricts at least one artery. The at least one artery encompasses one or more of, the aorta, the brachiocephalic artery, the right subclavian artery, the right common artery, the left common carotid artery, and the left subclavian artery. Moreover, the at least one artery encompasses any combination of, the aorta, the brachiocephalic artery, the right subclavian artery, the right common artery, the left common carotid artery, and the left subclavian artery. This embodiment further contemplates methods and systems that stimulate a venoarterial reflex constricting arterial blood flow in at least one artery that transmits blood to the brain and also constricting blood flow to at least one artery that does not transmit blood to the brain. The invention encompasses methods and procedures, that utilize partial constriction of venous blood flow to effect constriction of blood flow through an artery, and to re-direct blood in that artery to a different artery. The invention encompasses methods and procedures that utilize partial constriction (and not occlusion) of venous blood flow to effect constriction of blood flow through an artery, and to re-direct blood in that artery to a different artery, or to re-direct blood in that artery to a network of vessels. Moreover, the invention encompasses a method, a procedure, and a system that does not occlude venous blood flow, and that merely constricts venous blood flow, where the constriction of venous blood flow results in a venoarterial reflex that constricts at least one artery. In yet another aspect, the invention embraces a method, a procedure, and a system that does not occlude venous blood flow, and that merely constricts venous blood flow, where the constriction of venous blood flow results in a venoarterial reflex that constricts at least one artery and re-directs emboli away from the brain.

Detection and characterization of a region of the circulatory system that is subject to a venoarterial reflex can be accomplished by one or more of a number of techniques that do not limit the invention. In one aspect, the technique involves occluding a vein at a point immediately downstream of an organ, and monitoring constriction of an artery immediately upstream of the same organ. The presence of a constriction of the artery associated with the venous occlusion indicates the presence of the venoarterial reflex.

Without implying any limitation on the invention, the venoarterial reflex has been characterized as a local sympathetic reflex that causes precapillary resistance to increase in response to elevation of venous pressure. The results of this reflex is decreasing capillary flow (see, e.g., Delis, et al. (2000) Arch. Surg. 135:265-268). Venoarterial reflex occurs in a number of tissues and organs, such as the limbs (Bilecen, et al. (2004) Radiology 233:617-619; Delis, et al. (2000) Arch. Surg. 135:265-268); skin (Mork, et al. (2002) J. Invest. Dermatol. 118:699-703).

The instant teachings, among other things, encompass methods for preventing the transit of emboli, for blocking the transit of emboli, and for re-directing emboli. Without implying any limitation, the invention can be applied to emboli of unknown origin, emboli arising from an atherosclerotic lesion, emboli that are mural thrombi, emboli arising from unstable ulcerated plaques, emboli taking the form of atheromatous material, emboli that comprise gas bubbles, emboli taking the form of foreign bodies, such as synthetic microspheres. The invention can be used to prevent stroke or other pathological consequences of a single embolism, a plurality of emboli, or a shower of emboli, arising from medical procedures, such as surgery, and from mechanical procedures such as removing a clamp from the cardiovascular system (see, e.g., Mathew, et al. (2006) Ann. Thorac. Surg. 81:1644-1649, Barbut, et al. (1994) Stroke 25:2398-2402; Ghanem, et al. (2010) J. Am. College Cardiol. 55:1427-1432; Kahlert, et al. (2010) Circulation 121:870-878; Carter S. Martin RCG (2009) HPB 11:541-550; Sangro, et al. (2010) Am. J. Clin. Oncol. (epub ahead of print);

Microsphere-driven embodiments are contemplated by the present invention. Regarding synthetic microspheres, the invention provides novel methods for re-directing synthetic microspheres towards a desired or intended region of the body, for example, a region containing cancer, tumors, metastases, or new blood vessels induced by tumors. Synthetic microspheres, for example, those used in oncology are described (Tsai, et al. (2010) J. Vasc. Interv. Radiol. 21:1377-1384; Poggi, et al. (2011) Cardiovasc. Intervent. Radiol. 34 (Suppl. 2):S190-S194; Bower, et al. (2010) HPB (Oxford) 12:31-36). In another aspect, the invention provides novel methods for re-directing synthetic microspheres away from an undesired, or unintended region of the body. The present invention encompasses the combination of administering microspheres to the arterial side of an organ, with use of occlusion of a vein on the venous side of the organ, in order to re-direct the microspheres away from the organ. The microsphere embodiment of the invention encompasses use of fluorescent microspheres for use in real-time or fixed time monitoring the locations of the microspheres in the circulatory system (Brookes and Kaufman (2005) J. Physiol. 565:269-277).

The present invention encompasses a step where emboli are detected. Emboli can be detected, for example, by Doppler ultrasound, transcranial Doppler ultrasound, computed tomography pulmonary angiography, magnetic resonance imaging (MRI), lung scintigraphy, fluorescein angiography, by way of a Coulter counter, and histological methods (see, e.g., Levine (2004) Clin. Cardiol. 27 (Suppl. II) II-12-II-24; Nakamura, et al. (2008) Eur. J. Vasc. Endovasc. Surg. 35:96-101; Loubani, et al. (2006) J. Cardiothoracic Surg. 1:42).

The invention reduces the passage of emboli to 80% or less, to 70% or less, to 60% or less, to 50% or less, to 40% or less, to 30% or less, to 25% or less, to 20% or less, to 15% or less, to 10% or less, or to 5% or less, than the passage of emboli in absence of the invention. The passage that is reduced can be overall reduction of emboli of all sizes.

Emboli size-driven embodiments are encompassed by the invention. In yet another aspect, the present invention is configured to reduce the passage of emboli in the range of 1.0 mm to 0.001 mm, in the range of 0.5 mm to 0.001 mm, in the range of 0.4 mm to 0.001 mm, in the range of 0.3 mm to 0.001 mm, in the range of 0.2 mm to 0.001 mm, in the range of 0.1 mm to 0.001 mm, in the range of 0.05 mm to 0.001 mm, 0.025 mm to 0.001 mm, and the like. Very small emboli can have a diameter of 0.015 mm to 0.05 mm and up to 0.10 mm (see, e.g., Sangiorgi and Columbo (2003) Heart 89:990-992; Rapp, et al. (2003) Stroke 34:1976-1980). Emboli greater than 1.0 mm can occlude a major cerebral artery and cause a noticeable infarct, while emboli smaller than 0.5 mm can cause microinfarcts in the terminal cortical arterioles, as reviewed by Levine (2004) Clin. Cardiol. 27 (Suppl. 2), II12-II24.

In yet another aspect, the passage recited in the claims is reduced specifically reduced for emboli in the range of 1.0 mm or greater, 0.5 mm or greater, 0.4 mm or greater, 0.3 mm or greater, 0.2 mm or greater, 0.1 mm or greater, 0.05 mm or greater, 0.025 mm or greater, and so on. What is also encompassed, as recited in the claims, is passage that is reduced by 80% or less, 70% or less, 60% or less, 50% or less, 40% or less, 30% or less, 20% or less, 10% or less, 5% or less, specifically for emboli in the range of 0.025 mm to 0.05 mm, 0.05 mm to 0.1 mm, 0.05 to 0.2 mm, 0.1 mm to 0.2 mm, and the like.

Methods of the present invention are configured to prevent or reduce pathological consequences of a shower of emboli. In another aspect, the invention is configured to re-direct a shower of emboli. Mechanical procedures or surgical procedures on the cardiovascular system can provoke the release of emboli in a "shower of emboli," as disclosed, for example, by Abizaid (2008) Interventional Cardiology 37-40. Without implying any limitation, the invention transiently occludes a vein leaving the brain, thereby redirecting arterial blood that contains emboli away from the brain and to other locations in the body.

Anti-coagulant embodiments are likewise encompassed by the invention. The method of the invention can encompass administrating an anticoagulant, such as heparin, aspirin, or Warfarin, or by administering a thrombolytic agent, such as tissue plasminogen activator (tPA) or plasmin. Moreover, the method can exclude administering an anticoagulant, exclude administering a thrombolytic agent, or exclude administering both anticoagulant and thrombolytic agent.

Those skilled artisan also recognizes that guidance on occlusion devices, including balloons, is available. A balloon can be made of one or more of a number of materials, such as nylon or latex, as disclosed in U.S. Pat. No. 6,485,500 issued to Kokish, which is incorporated herein by reference. The balloon can be controlled by a console that electronically monitors the heart beat and expands and contracts the balloon in synchrony with the heart beat. The balloon can be filled with air or with a liquid such as saline (see, e.g., U.S. Pat. No. 5,330,451 of Gabbay.)

Transient occlusion can encompass 0.5 seconds or less, 1.0 sec or less, 5.0 sec or less, 10.0 sec or less, 15 sec or less, 20 sec or less, 25 sec or less, 30 sec or less, 35 sec or less 40 sec or less, 45 sec or less, 50 sec or less, 55 sec or less, 60 sec or less, 70 sec or less, 80 sec or less, 90 sec or less, 95 sec or less, 100 sec or less, 110 sec or less, 120 sec or less, 130 sec or less, 140 sec or less, 150 sec or less, 160 sec or less, 170 sec or less, 180 sec or less, 190 sec or less 200 sec or less, 210 sec or less, 220 sec or less, 230 sec or less, 240 sec or less, 250 sec or less, 260 sec or less, 270 sec or less, 280 sec or less, 290 sec or less, 300 sec or less, 1 minute or less, 2 min or less, min or less, 3 min or less, 4 min or less, and the like.

In another aspect, transient occlusion encompasses about 0.5 minutes, about 1.0 min, about 1.5 min, about 2.0 min, about 2.5 min, about 3.0 min, about 3.5 min, about 4.0 min, and the like.

In the context of constricting a vessel, constricting blood flow through a blood vessel can reduce blood flow by about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, and about 100%. Occlusion, by way of definition, constricts all blood flow past the point of occlusion.

The invention further embraces occlusions that are intermittent, for example, where fluctuations between maximal and minimal flow take the form of a square wave, sine wave, saw-tooth wave, and the like, and where the time frame between peaks of adjacent waves are about 10 minutes, about 5 min, about 2 min, about 90 seconds, about 60 seconds, about 30 seconds, 20 seconds, about 15 seconds, about ten seconds, about 8 seconds, about five seconds, about two seconds, about one second, about 0.8 sec, about 0.5 sec, about 0.2 sec, about 0.1 sec, about 0.8 sec, about 0.5 sec, about 0.2 sec, about 0.1 sec, about 0.08 sec, about 0.05 sec, about 0.02 sec, about 0.01 sec, and the like.

The following concerns organ embodiments. The methods, procedures, systems, devices, and compositions, of the present invention can be practiced, without limitation, with a number of organs and tissues, including brain, eye, heart, spleen, bone marrow, lung, kidney, pancreas, ovary, gastrointestinal tract, adipose tissue, cutaneous tissue, skin, a gland, such as adrenal gland, stomach, duodenum, ileum, colon, or one or more limbs, for example, the hand, forearm, arm, thigh, leg, and additionally, pathological tissues, such as one or more tumors, one or more cancers, metastases, micrometastases, cysts, an infected organ, an infected tissue, a virally-infected organ or tissue, a bacterially-infected organ or tissue, an inflamed organ or tissue, and the like. In one aspect, the invention of capable of directing of blood, or blood and emboli, away from one or more of these organs and tissues. In another aspect, the invention is capable of directing blood, or blood and emboli, towards one or more of these organs and tissues.

The invention contemplates occluding blood flow through a vein, partially or completely blocking blood flow through a vein, by way of a balloon catheter, a cuff devices, a mechanical umbrella, and in a general aspect a device made of any non-porous material, a vascular clamp applied to the outside of a vein, and pressure applied to the outside of the body, for example, to a limb. Reducing blood venous flow by applying pressure by way of a tourniquet is disclosed, for example, by Hampson and Piantadosi (1988) J. Appl. Physiol. 64:2449-2457.

Balloon catheters and methods of use including methods for controlling volume and pressure are described, for example, in U.S. Pat. No. 7,972,299 issued to Carter, et al; U.S. Pat. Nos. 7,914,643 and 7,967,781 of Simpson, et al, U.S. Pat. No. 7,959,667 of Ta, et al; U.S. Pat. No. 7,951,259 of Duchamp, et al; U.S. Pat. No. 7,909,794 issued to Briscoe, et al; U.S. Pat. No. 7,909,844 of Alkhatib, et al; U.S. Pat. No. 7,896,840 of Spencer, et al; and U.S. Pat. No. 6,485,500 issued to Kokish, and so on. Each of these patents is hereby incorporated by reference, as if fully set forth herein.

Without implying any limitation, the methods of the present invention encompass methods for preventing the venous flow of blood from dislodging an occluding balloon. In one aspect, this method causes cardiac fibrillation, that is, rapid pacing of the heart, to accomplish this end. In another aspect, the method of the invention encompasses use of a balloon catheter for substantially blocking the flow of blood, thereby preventing the venous flow of blood from dislodging an occluding balloon (see, for example, the balloon catheter with two seating members of U.S. Pat. No. 5,458,574 issued to Peters). Typically, the maximal time interval for causing fibrillation is about 30 seconds. Often, the maximum time interval for causing fibrillation with contemporaneous occlusion of the venous flow is also 30 seconds. In a further embodiment, the method of the invention does not use a fibrillator to prevent blood from dislodging the occluding device, e.g., an occluding balloon or inflatable cuff.

Cuff devices for obstructing blood flow are disclosed, for example, in U.S. Pat. Nos. 5,433,700 and 5,762,624, both issued to Peters, and U.S. Pat. No. 5,814,097 issued to Sterman, et al, each of which are incorporated by reference, as if fully set forth herein. In another aspect, the methods of the present invention encompass using a mechanical umbrella for occluding a blood vessel, for inducing a venoarterial reflex, for preventing the flow of emboli into a vein, and the like. Mechanical umbrellas for use in the circulatory system are disclosed, for example, in U.S. Appl. No. 20020165581 of Brucker (sole) and U.S. Pat. No. 6,596,013 issued to Yang et al, both of which are incorporated by reference in their entirety.

Controllers configured for controlling balloon inflation or deflation are disclosed, for example, in U.S. Pat. No. 7,674,240 of Webler, et al; U.S. Pat. No. 7,285,120 issued to Im, et al; U.S. Pat. Nos. 6,245,008 and 5,817,001 of Leschinsky, et al; 20100063534 of Kugler, et al; U.S. Pat. No. 7,363,072 issued to Movahed, and U.S. Pat. No. 7,048,702 of Hui. Each of these is incorporated herein by reference, as if fully set forth herein. Another aspect, the invention provides manual control in place of, or in addition to, for example, an electrical controller.

Controllers suitable for controlling balloon inflation are also described, for example, by Savage, et al. (1999) Ann Thorac. Surg. 68:768-774; Olbrich, et al. (2006) Physiol Meas.; 27:213-2231; Danchin, et al. (2007) Adv. Cardiol. 44:139-149; Shehab, et al. (2008) Cardiovasc. Intervent. Radiol. 31:149-157; Unverdorben, et al. (1997) Comput. Biomed. Res. 30:403-413.

Combinations involving filters are encompassed by the invention. Filters for use in filtering emboli, fragments of atherosclerotic plaque, calcium particles, tissue fragments, and the like, may be used with the present invention. The composition, pore size, and methods of use of filters are disclosed, for example, in U.S. Pat. No. 7,323,001 issued to Clubb, et al.; Kinney (2003) J. Vascular Interventional Radiol. 14:425-440.

Without implying any limitation, the present invention provides methods for improving the emboli-limiting effect of a filter, by combining use of a filter with occluding a vein at the downstream side of an organ, thereby stimulating arterial flow constriction at the arterial side of the organ, resulting in re-direction of blood an any emboli away from the organ. In one aspect, the method comprises occluding a vein at the downstream side of an organ, thereby stimulating arterial flow constriction at the arterial side of the organ, resulting in re-direction of blood an any emboli away from the organ, where a subject already comprises a filter. In another aspect, the method comprises two steps, where the two steps can be practiced in either order: (1) Implanting the filter and (2) Occluding a vein at the downstream side of an organ, thereby stimulating arterial flow constriction at the arterial side of the organ, resulting in re-direction of blood an any emboli away from the organ, where a subject already comprises a filter. In one aspect, the filter resides in the vein. In another aspect, the filter resides in the artery. In yet another aspect, filters reside in both the artery and vein.

According to yet other aspects, the invention optionally includes a distal arterial pressure gauge for monitoring upstream pressure, as well as a proximal venous pressure gauge for monitoring downstream pressure. Pressure gauges are also embraced by the present invention. Arterial pressure gauges, venous pressure gauges, and methods for use are disclosed, for example, in U.S. Pat. No. 6,843,779 issued to Andrysiak, et al, U.S. Pat. No. 4,846,787 issued Aall-Flood, et al, and U.S. Publ. No. 2003/0186203 of Aboud, U.S. Pat. No. 6,146,354 of Beil, and U.S. Publ. No. 2008/0294070 of Kinori.

Components for the methods and devices of the present invention are available, for example, from any known major medical device company, for example, Medtronic of Minneapolis, Minn.; Advanced Cardiovascular Systems in Santa Clara, Calif.; Baxter International of Deerfield, Ill.; Abbott Laboratories at Abbott Park, Ill., Edwards Lifesciences, Irvine, Calif. and Boston Scientific of Natick, Mass.

The method of the present invention can be used in conjunction with treatments that potentially result in emboli, or that actually result in emboli, for example, carotid endarterectomy, cardioversion for atrial fibrillation, operative repair of thoracic aortic aneurysms, coronary artery bypass grafting, aortic valve surgery, mitral valve surgery, placement of shunt, removal of a vascular clamp, and the like. WO 95/16476 of Stevens and U.S. Pat. No. 5,330,451 of Gabbay, disclose that debris, such as tissue debris or calcium particles, can be released into the circulation during cardiovascular. U.S. Pat. No. 5,458,574 of Machold reveals that applying or removing clamps can generate emboli that can travel into the brachiocephalic artery, the carotid artery, or the subclavian artery, resulting in stroke.

Saphenous vein grafts are a special concern, as disease in these grafts is typically a very friable plaque that can dislodge quite easily. The mere act of passing the interventional devices through these vessels can dislodge embolic material. When a physician performs a procedure in the saphenous vein, a filtering system may be used to capture the friable plaque. See, for example, U.S. Pat. No. 6,558,405, issued to McInnes, which is incorporated herein in its entirety. The invention provides a method and system for redirecting blood, and for re-directing blood that contains emboli, away from the brain, where the emboli are expected to arise from, or where the emboli actually arise from, a saphenous vein graft or from a procedure involving a saphenous vein graft.

The present invention used in conjunction with these, or other treatments, can re-direct emboli away from the brain region subtended by the occluded vein. In one aspect, the invention re-directs at least 5% of emboli away from the brain, at least 10% of emboli, at least 20% of emboli, at least 30% of emboli, 40% or greater of the emboli, at least 50% of emboli, at least 60% of emboli, 70% or more of emboli, at least 80% of emboli, 90% or greater of the emboli, 95% or more of the emboli, and the like.

The invention can be used in the context of surgical procedures where anticoagulant or thromboplastic therapy is required, as disclosed, for example, in WO 95/16476 of Stevens. U.S. Pat. No. 6,866,650 of Stevens, et al., Goldhaber, et al. (2004) Circulation 109:2712-2715; Groom, et al. (2009) Circ. Cardiovasc. Qual. Outcomes 2:191-198.

EXAMPLES

Referring to FIG. 1, percutaneous internal jugular vein catheterization is used to introduce an inflatable balloon that is capable of occluding this vein. The balloon is deliberately and intermittently inflated before manipulations of the aorta, in particular, before manipulations expected to generate emboli, such as particles of atherosclerotic plaque. These manipulations include removal of an aortic cross clamp and partial occlusion clamp. By way of the balloon, the jugular venous pressure is increased transiently, resulting in a venoarterial reflex that constricts blood flow from the aorta to the brain. Alternatively, or in addition, an inflatable balloon can be implanted in and used in a brachiocephalic vein or in the superior vena cava. Where balloons are used in more than one vein, the occlusions can be timed to be simultaneous, or they can be staggered in time.

Figure 2:
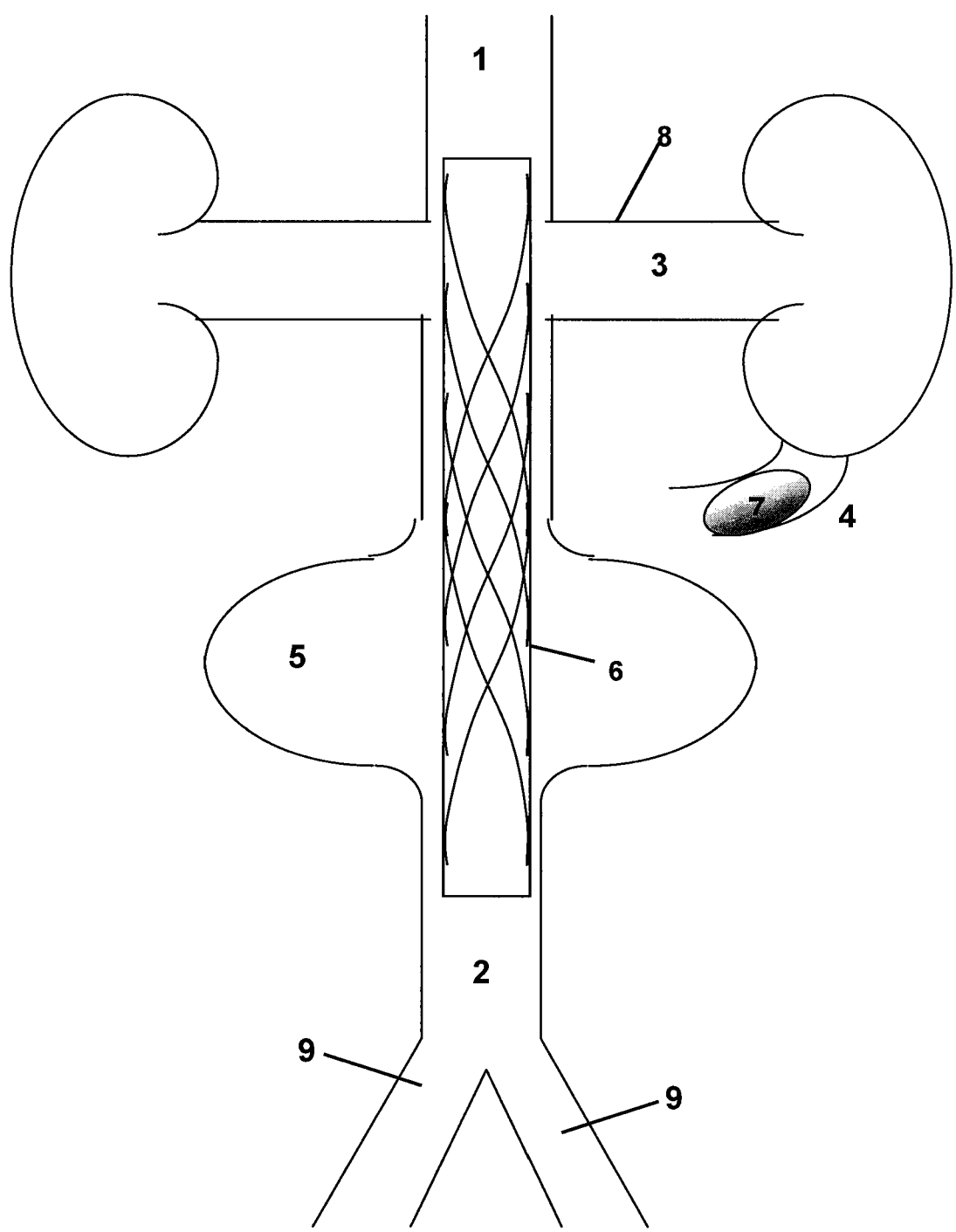
FIG. 2. Venoarterial reflex preventing passage of emboli to kidney. (1) Thoracic aorta; (2) Abdominal aorta; (3) Renal artery; (4) Renal vein; (5) Abdominal aortic aneurysm; (6) Stent; (7) Occluding balloon; (8) Venoarterial reflex causes constriction; (9) The reflex-induced constriction re-directs blood and emboli, towards or through the indicated vessels.

FIG. 2 shows a stent that bridges an abdominal aortic aneurysm. A balloon can be inserted in the renal vein, and inflated to cause an occlusion, at the time the stent is implanted, at the time the stent is being maintained, or at the time the stent is being removed. The balloon is inflated transiently, and kept inflated, during the brief time frame when emboli are expected to be generated. The venoarterial reflex constricts the renal artery, and causes blood in the aorta, along with emboli, to be re-directed, for example, through the common ileac artery. The result is that emboli are re-directed through the common ileac artery.

Figure 3:
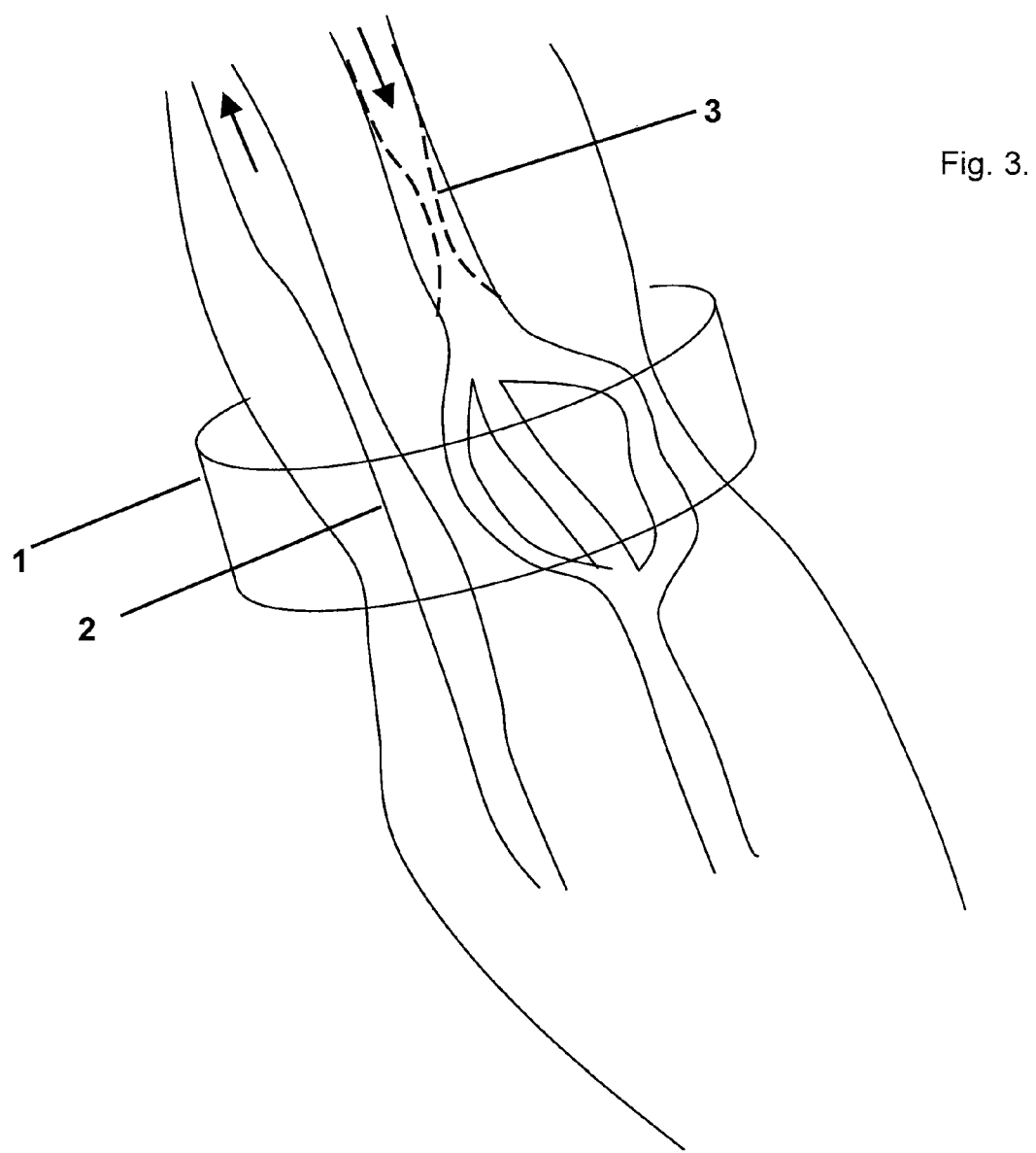
FIG. 3. Venoarterial reflex in the arm. (1) Cuff compressing outside of arm; (2) Pressure of cuff occludes vein, provoking venoarterial reflex; (3) Venoarterial reflex stimulates constriction of artery.

FIG. 3 depicts the venoarterial reflex in an arm, where a vein is occluded by external pressure from a cuff or tourniquet. Venous blood in the arm, as shown, has a pressure of about 20 mm Hg, while arterial blood has a pressure of about 100 mm Hg. The cuff in the figure directs pressure at 35 mm Hg. Consequently, venous flow is occluded (stopped) while arterial blood continues. The resulting venoarterial reflex causes a constriction in the artery, as shown. This constriction impairs continued flow of this arterial blood to the capillaries and to the venous circulation.

While methods, devices, compositions, and the like, have been described in terms of what are presently considered to be the most practical and preferred implementations, it is to be understood that the disclosure need not be limited to the disclosed implementations. It is intended to cover various modifications and similar arrangements included within the spirit and scope of the claims, the scope of which should be accorded the broadest interpretation so as to encompass all such modifications and similar structures. The present disclosure includes any and all implementations of the following claims. It is understood that the term, present invention, in the context of a description of a component, characteristic, or step, of one particular embodiment of the invention, does not imply or mean that all embodiments of the invention comprise that particular component, characteristic, or step.

It should also be understood that a variety of changes may be made without departing from the essence of the disclosure. Such changes are also implicitly included in the description. They still fall within the scope of this disclosure. It should be understood that this disclosure is intended to yield a patent covering numerous aspects of the disclosure both independently and as an overall system and in both method and apparatus modes.

Further, each of the various elements of the disclosure and claims may also be achieved in a variety of manners. This disclosure should be understood to encompass each such variation, be it a variation of an implementation of any apparatus implementation, a method or process implementation, or even merely a variation of any element of these.

Particularly, it should be understood that as the disclosure relates to elements of the disclosure, the words for each element may be expressed by equivalent apparatus terms or method terms—even if only the function or result is the same.

Such equivalent, broader, or even more generic terms should be considered to be encompassed in the description of each element or action. Such terms can be substituted where desired to make explicit the implicitly broad coverage to which this disclosure is entitled.

It should be understood that all actions may be expressed as a means for taking that action or as an element which causes that action.

Similarly, each physical element disclosed should be understood to encompass a disclosure of the action which that physical element facilitates.

Any patents, publications, or other references mentioned in this application for patent are hereby incorporated by reference. In addition, as to each term used it should be understood that unless its utilization in this application is inconsistent with such interpretation, common dictionary definitions should be understood as incorporated for each term and all definitions, alternative terms, and synonyms such as contained in at least one of a standard technical dictionary recognized by artisans and the Random House Webster's Unabridged Dictionary, latest edition are hereby incorporated by reference.

Finally, all referenced listed in the Information Disclosure Statement or other information statement filed with the application are hereby appended and hereby incorporated by reference; however, as to each of the above, to the extent that such information or statements incorporated by reference might be considered inconsistent with the patenting of this/these disclosure(s), such statements are expressly not to be considered as made by the applicant(s).

In this regard it should be understood that for practical reasons and so as to avoid adding potentially hundreds of claims, the applicant has presented claims with initial dependencies only.

Support should be understood to exist to the degree required under new matter laws—including but not limited to United States Patent Law 35 USC 132 or other such laws—to permit the addition of any of the various dependencies or other elements presented under one independent claim or concept as dependencies or elements under any other independent claim or concept.

To the extent that insubstantial substitutes are made, to the extent that the applicant did not in fact draft any claim so as to literally encompass any particular implementation, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would have literally encompassed such alternative implementations.

Further, the use of the transitional phrase "comprising" is used to maintain the "open-end" claims herein, according to traditional claim interpretation. Thus, unless the context requires otherwise, it should be understood that the term "compromise" or variations such as "comprises" or "comprising", are intended to imply the inclusion of a stated element or step or group of elements or steps but not the exclusion of any other element or step or group of elements or steps.

Such terms should be interpreted in their most expansive forms so as to afford the applicant the broadest coverage legally permissible.

What is claimed is:

1. A method for reducing the flow of blood entering an organ or tissue, comprising transiently occluding a vein that carries blood out of the organ or tissue, wherein the occluding raises the blood pressure in the vein, wherein the raise in blood pressure stimulates a venoarterial reflex, wherein the reflex reduces the passage of blood through an artery or arteriole entering the organ or tissue, and re-directs blood away from the organ or tissue, wherein the artery or arteriole comprises at least one embolus, and wherein the method re-directs the at least one embolus away from the organ or tissue.

2. The method of claim 1, wherein the occluding comprises a device, wherein the device comprises a non-porous material, and wherein the device is non-porous to blood flowing from an upstream side of the device to a downstream side of the device.

3. The method of claim 1, wherein the occluding is accomplished with a balloon located in the lumen of the vein, a device comprising an occluding cuff located in the lumen of the vein, a device that clamps the outside of the vein, manual contact that presses on the outside of the vein, or a tourniquet that constricts a limb.

4. The method of claim 1, wherein the occluding is not accomplished with a device comprising a balloon.

5. The method of claim 1, wherein the artery or arteriole comprises at least one embolus, and wherein the method re-directs the at least one embolus away from the organ or tissue, and wherein the embolus comprises a blood clot, a fragment of atherosclerotic plaque, debris from surgery, as gas bubble, a synthetic microsphere, or an iatrogenic consequence of a medical procedure.

6. The method of claim 1, that further includes a medical procedure that comprises carotid endarterectomy, cardioversion for atrial fibrillation, repair of thoracic aortic aneurysm, coronary artery bypass grafting, aortic valve surgery, mitral valve surgery, clamp removal, or iatrogenic physical trauma to the cardiovascular system.

7. The method of claim 1, where the artery comprises a saphenous vein graft.

8. The method of claim 1, wherein the organ is the brain or kidney.

9. The method of claim 1, that comprises transient occluding of the superior vena cava or jugular vein, wherein the venoarterial reflex constricts blood flow in one or more of the aorta, subclavian artery, brachiocephalic artery, subclavian artery, and reduces blood flow to the brain.

10. The method of claim 1, wherein the occluding is accomplished with a device comprising a non-porous material that is non-porous to blood flowing from an upstream side of the device to a downstream side of the device, wherein the device is located in the lumen of the vein downstream of the heart, wherein blood flow in the vein introduces an instability of the position or fit of the device within the lumen, and wherein the method further comprises stabilizing the device by fibrillating the heart or by reducing the volume or rate of the blood flow that enters the heart.

11. The method of claim 1, that comprises transient occluding of the renal vein, wherein a venoarterial reflex constricts blood flow in the aorta, and wherein the reflex reduces blood flow, or blood flow and at least one embolus, to at least one kidney.

12. The method of claim 1, wherein there is a region of occlusion or a point of occlusion created by the occluding a vein, wherein the method further includes use of a gauge that monitors blood pressure in a region of the circulatory system between the organ and the region or point of occlusion.

13. The method of claim 1, that comprises use of an occluding balloon that transiently occludes the vein, wherein the balloon is coupled to a controller that monitors venous pressure, and wherein the controller deflates the balloon if the pressure is too high or inflates the balloon if the pressure is too low.

14. The method of claim 1, that includes using a pressure safety-release valve for reducing venous pressure if the pressure is too high.

15. The method of claim 1, that includes a monitor that monitors the frequency of emboli, and wherein there is a controller that controls a balloon that occludes a vein, wherein the controller maintains inflation of the balloon, or increases inflation of the balloon, when the controller detects an elevated frequency of emboli.

16. The method of claim 1, further comprising using, maintaining, or implanting, a filter in an artery or vein that traps emboli, or administering an anti-coagulant or thrombolytic agent.

17. A method for reducing the passage of emboli into an organ or tissue, comprising transiently occluding a vein that carries blood out of the organ or tissue, wherein the occluding raises the blood pressure in the vein, wherein the raised blood pressure in the vein stimulates a venoarterial reflex that constricts an artery or arteriole carrying blood, or blood and emboli, into the organ or tissue, resulting in a re-directing of blood, or blood and emboli, away from the organ or tissue and through at least one artery or arteriole that does not carry blood to the organ or tissue, wherein the artery or arteriole comprises at least one embolus, and wherein the method re-directs the at least one embolus away from the organ or tissue.

18. The method of claim 17, wherein the occluding comprises a device, wherein the device comprises a non-porous material, and wherein the device is non-porous to blood flowing from an upstream side of the device to a downstream side of the device.

19. The method of claim 17, wherein the occluding is accomplished with a balloon located in the lumen of the vein, a device comprising an occluding cuff located in the lumen of the vein, a device that clamps the outside of the vein, manual contact that presses on the outside of the vein, or a tourniquet that constricts a limb.

20. The method of claim 17, wherein the occluding is not accomplished with a device comprising a balloon.

21. The method of claim 17, wherein the artery or arteriole comprises at least one embolus, and wherein the method re-directs the at least one embolus away from the organ or tissue, and wherein the embolus comprises a blood clot, a fragment of atherosclerotic plaque, debris from surgery, a gas bubble, a synthetic microsphere, or an iatrogenic consequence of a medical procedure.

22. The method of claim 17, that further includes a medical procedure that comprises carotid endarterectomy, cardioversion for atrial fibrillation, repair of thoracic aortic aneurysm, coronary artery bypass grafting, aortic valve surgery, mitral valve surgery, clamp removal, or iatrogenic physical trauma to the cardiovascular system.

23. The method of claim 17, where the artery comprises a saphenous vein graft.

24. The method of claim 17, wherein the organ is the brain or kidney.

25. The method of claim 17, that comprises transient occluding of the superior vena cava or jugular vein, wherein the venoarterial reflex constricts blood flow in one or more of the aorta, subclavian artery, brachiocephalic artery, subclavian artery, and reduces blood flow to the brain.

26. A method for preventing or mitigating emboli-dependent stroke, ischemic attack, neurocognitive deficit, or Alzheimer's disease, comprising transiently occluding a vein that delivers blood out of the brain, wherein the occluding raises blood pressure in the vein, wherein the raised blood pressure in the vein stimulates a venoarterial reflex that constricts an artery that delivers blood to the brain where the artery includes emboli, resulting in a re-directing of emboli away from the brain and to the extracranial systemic circulation.

27. The method of claim 26, wherein the vein is the superior vena cava or jugular vein.

28. The method of claim 26, wherein the vein is not the superior vena cava and not the jugular vein.

29. The method of claim 26, wherein the artery comprises the carotid artery or an intracranial artery of the brain.

* * * * *

UNITED STATES PATENT AND TRADEMARK OFFICE
CERTIFICATE OF CORRECTION

PATENT NO. : 8,449,565 B2  Page 1 of 1
APPLICATION NO. : 13/188408
DATED : May 28, 2013
INVENTOR(S) : Francis Duhay It is certified that error appears in the above-identified patent and that said Letters Patent is hereby corrected as shown below:

In the Specification:

In Column 2, line 15, "generation blood clots" should be --generation of blood clots--

In Column 2, line 36, "limit" should be --limited--

In Column 9, immediately below line 27, insert a line that includes only the words --Detailed Description--

In Column 9, line 37, "arteriolar" should be --arteriole--

In the Claims:

In Column 19, Claim 5, line 5, "as gas bubble" should be --a gas bubble--

Signed and Sealed this
Sixth Day of August, 2013

Teresa Stanek Rea
*Acting Director of the United States Patent and Trademark Office*

UNITED STATES PATENT AND TRADEMARK OFFICE
CERTIFICATE OF CORRECTION

PATENT NO. : 8,449,565 B2  
APPLICATION NO. : 13/188408  
DATED : May 28, 2013  
INVENTOR(S) : Francis Duhay Page 1 of 1

It is certified that error appears in the above-identified patent and that said Letters Patent is hereby corrected as shown below:

In the Specification:

In Column 2, line 15, "generation blood clots" should be --generation of blood clots--

In Column 2, line 36, "limit" should be --limited--

In Column 9, immediately below line 27, insert a line that includes only the words --Detailed Description--

In Column 9, line 37, "arteriolar" should be --arteriole--

In the Claims:

Column 19, lines 27-28 (Claim 5, lines 5-6) "as gas bubble" should be --a gas bubble--

This certificate supersedes the Certificate of Correction issued August 6, 2013.

Signed and Sealed this
Twenty-seventh Day of August, 2013

Teresa Stanek Rea
*Acting Director of the United States Patent and Trademark Office*